United States Patent
Deutsch et al.

(10) Patent No.: US 8,003,377 B2
(45) Date of Patent: *Aug. 23, 2011

(54) PICO LITER WELL HOLDING DEVICE AND METHOD OF MAKING THE SAME

(75) Inventors: Mordechai Deutsch, Moshav Olesh-Doar-Na Lev HaSharon (IL); Assaf Deutsch, Tzfaria (IL)

(73) Assignee: Seng Enterprises Ltd., Larnaca (CY)

( * ) Notice: Subject to any disclaimer, the term of this patent is extended or adjusted under 35 U.S.C. 154(b) by 0 days.

This patent is subject to a terminal disclaimer.

(21) Appl. No.: 12/890,668

(22) Filed: Sep. 26, 2010

(65) Prior Publication Data

US 2011/0014688 A1    Jan. 20, 2011

Related U.S. Application Data

(63) Continuation of application No. 11/940,996, filed on Nov. 15, 2007, which is a continuation-in-part of application No. 10/561,839, filed as application No. PCT/IL2004/000571 on Jun. 27, 2004, application No. 11/940,996, which is a continuation-in-part of application No. PCT/IL2006/001487, filed on Dec. 26, 2006.

(60) Provisional application No. 60/544,357, filed on Feb. 17, 2004, provisional application No. 60/544,356, filed on Feb. 17, 2004, provisional application No. 60/517,073, filed on Nov. 5, 2003, provisional application No. 60/517,084, filed on Nov. 5, 2003, provisional application No. 60/488,408, filed on Jul. 21, 2003, provisional application No. 60/482,437, filed on Jun. 26, 2003, provisional application No. 60/754,216, filed on Dec. 28, 2005.

(51) Int. Cl.
*C12M 3/00* (2006.01)
*C12M 1/34* (2006.01)
*C12M 1/22* (2006.01)

(52) U.S. Cl. .................... 435/288.5; 435/305.2

(58) Field of Classification Search ............... 435/288.5, 435/305.2
See application file for complete search history.

(56) References Cited

U.S. PATENT DOCUMENTS 3,558,387 A    1/1971    Bassemir et al.
(Continued)

FOREIGN PATENT DOCUMENTS

DE            4132379            4/1993
(Continued)

OTHER PUBLICATIONS

Official Action Dated Feb. 5, 2007 From the US Patent and Trademark Office Re.: U.S. Appl. No. 10/916,380.
Official Action Dated Feb. 19, 2008 From the US Patent and Trademark Office Re.: U.S. Appl. No. 10/492,531.
Official Action Dated Sep. 20, 2007 From the US Patent and Trademark Office Re.: U.S. Appl. No. 10/492,531.
Official Action Dated Jan. 25, 2007 From the US Patent and Trademark Office Re.: U.S. Appl. No. 10/492,531.

(Continued)

*Primary Examiner* — Walter D Griffin
*Assistant Examiner* — Lydia Edwards

(57) ABSTRACT

The present invention broadly comprises a holding device for studying cells comprising at least one cavity adapted to receive cells in a medium consisting essentially of water, the cavity having a substrate and a generally inert wall, wherein the substrate includes a surface for receiving the medium, and wherein the surface includes a multiplicity of pico liter wells and is characterized in that the substrate is substantially translucent and has a refractive index equal to the refractive index of the medium. The invention further comprises a method of making the holding device comprising providing a carrier plate, applying an adhesive layer to the carrier plate, depositing a curable substrate on the adhesive layer, applying a second layer of adhesive to the substrate, attaching a wall structure to the second layer of adhesive, forming a multiplicity of pico liter wells in the substrate, curing the substrate, and removing the template.

26 Claims, 4 Drawing Sheets

U.S. PATENT DOCUMENTS

| | | | |
|---|---|---|---|
| 4,207,554 A | 6/1980 | Resnick et al. |
| 4,308,351 A | 12/1981 | Leighton et al. |
| 4,684,538 A | 8/1987 | Klemarczyk |
| 4,716,101 A | 12/1987 | Thompson |
| 4,729,949 A | 3/1988 | Weinreb et al. |
| 4,894,343 A | 1/1990 | Tanaka et al. |
| 5,059,266 A | 10/1991 | Yamane et al. |
| 5,204,055 A | 4/1993 | Sachs et al. |
| 5,272,081 A | 12/1993 | Weinreb et al. |
| 5,324,591 A | 6/1994 | Georger et al. |
| 5,395,588 A | 3/1995 | North, Jr. et al. |
| 5,428,451 A | 6/1995 | Lea et al. |
| 5,506,141 A | 4/1996 | Weinreb et al. |
| 5,525,800 A | 6/1996 | Sanghera et al. |
| 5,612,184 A | 3/1997 | Rosson |
| 5,627,045 A | 5/1997 | Bochner et al. |
| 5,650,323 A | 7/1997 | Root |
| 5,707,869 A | 1/1998 | Wolf et al. |
| 5,854,684 A | 12/1998 | Stabile et al. |
| 5,905,031 A | 5/1999 | Kuylen et al. |
| 5,910,287 A | 6/1999 | Cassin et al. |
| 6,025,129 A | 2/2000 | Nova et al. |
| 6,027,695 A | 2/2000 | Oldenburg et al. |
| 6,046,426 A | 4/2000 | Jeantette et al. |
| 6,066,285 A | 5/2000 | Kumar |
| 6,103,479 A | 8/2000 | Taylor |
| 6,117,612 A | 9/2000 | Halloran et al. |
| 6,206,672 B1 | 3/2001 | Grenda |
| 6,228,437 B1 | 5/2001 | Schmidt |
| 6,238,614 B1 | 5/2001 | Yang et al. |
| 6,329,195 B1 | 12/2001 | Pfaller |
| 6,333,192 B1 | 12/2001 | Petitte et al. |
| 6,338,964 B1 | 1/2002 | Matanguihan et al. |
| 6,342,384 B1 | 1/2002 | Chung et al. |
| 6,344,354 B1 | 2/2002 | Webster et al. |
| 6,345,115 B1 | 2/2002 | Ramm et al. |
| 6,372,494 B1 | 4/2002 | Naughton et al. |
| 6,376,148 B1 | 4/2002 | Liu et al. |
| 6,377,721 B1 | 4/2002 | Walt et al. |
| 6,378,527 B1 | 4/2002 | Hungerford et al. |
| 6,383,810 B2 | 5/2002 | Fike et al. |
| 6,403,369 B1 | 6/2002 | Wood |
| 6,410,309 B1 | 6/2002 | Barbera-Guillem et al. |
| 6,413,680 B1 | 7/2002 | Watanabe et al. |
| 6,413,744 B1 | 7/2002 | Morris et al. |
| 6,413,746 B1 | 7/2002 | Field |
| 6,455,310 B1 | 9/2002 | Barbera-Guillem et al. |
| 6,465,000 B1 | 10/2002 | Kim |
| 6,465,205 B2 | 10/2002 | Hicks, Jr. |
| 6,468,788 B1 | 10/2002 | Marotzki |
| 6,479,252 B1 | 11/2002 | Barbera-Guillem et al. |
| 6,485,690 B1 | 11/2002 | Pfost et al. |
| 6,489,144 B1 | 12/2002 | Lau |
| 6,492,148 B1 | 12/2002 | van Loon et al. |
| 6,492,163 B1 | 12/2002 | Yoo et al. |
| 6,495,340 B2 | 12/2002 | Huberman et al. |
| 6,506,598 B1 | 1/2003 | Andersen et al. |
| 6,511,430 B1 | 1/2003 | Sherar et al. |
| 6,528,286 B1 | 3/2003 | Ryll |
| 6,544,788 B2 | 4/2003 | Singh |
| 6,555,365 B2 | 4/2003 | Barbera-Guillem et al. |
| 6,569,422 B1 | 5/2003 | van Loon et al. |
| 6,588,586 B2 | 7/2003 | Abasolo et al. |
| 6,589,765 B1 | 7/2003 | Choi et al. |
| 6,593,101 B2 | 7/2003 | Richards-Kortum et al. |
| 6,593,140 B1 | 7/2003 | Field |
| 6,610,516 B1 | 8/2003 | Andersen et al. |
| 6,627,426 B2 | 9/2003 | Biddle et al. |
| 6,632,619 B1 | 10/2003 | Harrison et al. |
| 6,635,448 B2 | 10/2003 | Bucciarelli et al. |
| 6,642,050 B1 | 11/2003 | Goto et al. |
| 6,645,757 B1 | 11/2003 | Okandan et al. |
| 6,649,408 B2 | 11/2003 | Bailey et al. |
| 6,653,124 B1 | 11/2003 | Freeman |
| 6,660,501 B2 | 12/2003 | Field |
| 6,667,034 B2 | 12/2003 | Palsson et al. |
| 6,670,180 B2 | 12/2003 | Block |
| 6,670,184 B2 | 12/2003 | Chiarello et al. |
| 6,673,591 B2 | 1/2004 | Lau |
| 6,686,190 B2 | 2/2004 | Lau |
| 6,689,594 B1 | 2/2004 | Hänni et al. |
| 6,692,961 B1 | 2/2004 | Judd et al. |
| 7,118,910 B2 | 10/2006 | Unger et al. |
| 7,139,415 B2 | 11/2006 | Finkbeiner |
| 7,169,578 B2 | 1/2007 | Wang et al. |
| 7,323,305 B2 | 1/2008 | Leamon et al. |
| 7,354,733 B2 | 4/2008 | Bukshpan et al. |
| 7,403,647 B2 | 7/2008 | Deutsch et al. |
| 7,405,071 B2 | 7/2008 | Deutsch |
| 7,888,110 B2 | 2/2011 | Deutsch et al. |
| 2002/0052003 A1 | 5/2002 | Alberte et al. |
| 2002/0064885 A1 | 5/2002 | Bedingham et al. |
| 2002/0106715 A1 | 8/2002 | Huberman et al. |
| 2002/0150909 A1 | 10/2002 | Stuelpnagel et al. |
| 2002/0173033 A1 | 11/2002 | Hammerick et al. |
| 2002/0182627 A1 | 12/2002 | Wang et al. |
| 2002/0187074 A1 | 12/2002 | O'Connor et al. |
| 2002/0189374 A1 | 12/2002 | DeSilets et al. |
| 2003/0017079 A1 | 1/2003 | Hahn et al. |
| 2003/0030184 A1 | 2/2003 | Kim et al. |
| 2003/0032204 A1 | 2/2003 | Walt et al. |
| 2003/0036188 A1 | 2/2003 | Kim et al. |
| 2003/0059764 A1 | 3/2003 | Ravkin et al. |
| 2003/0082632 A1 | 5/2003 | Shumate |
| 2003/0082818 A1 | 5/2003 | Bahnson et al. |
| 2003/0104494 A1 | 6/2003 | Ravkin et al. |
| 2003/0113833 A1 | 6/2003 | Oka et al. |
| 2003/0124716 A1 | 7/2003 | Hess et al. |
| 2003/0189850 A1 | 10/2003 | Sasaki et al. |
| 2003/0211458 A1 | 11/2003 | Sunray et al. |
| 2004/0053354 A1 | 3/2004 | Ikawa et al. |
| 2004/0091397 A1 | 5/2004 | Picard |
| 2004/0118757 A1 | 6/2004 | Terstappen et al. |
| 2004/0216835 A1 | 11/2004 | Tanner et al. |
| 2004/0235143 A1 | 11/2004 | Sasaki et al. |
| 2004/0241783 A1 | 12/2004 | Papkovsky et al. |
| 2005/0014201 A1 | 1/2005 | Dcutsch |
| 2005/0026299 A1 | 2/2005 | Bhattacharjee et al. |
| 2005/0064524 A1 | 3/2005 | Deutsch et al. |
| 2005/0170498 A1 | 8/2005 | Dolley et al. |
| 2005/0277125 A1 | 12/2005 | Benn et al. |
| 2006/0041384 A1 | 2/2006 | Kermani et al. |
| 2006/0057557 A1 | 3/2006 | Deutsch et al. |
| 2006/0154233 A1 | 7/2006 | Deutsch |
| 2006/0240548 A1 | 10/2006 | Deutsch et al. |
| 2007/0105089 A1 | 5/2007 | Deutsch |
| 2007/0141555 A1 | 6/2007 | Deutsch |
| 2007/0154357 A1 | 7/2007 | Szlosek |
| 2007/0178607 A1 | 8/2007 | Prober et al. |
| 2007/0292837 A1 | 12/2007 | Deutsch et al. |
| 2008/0003142 A1 | 1/2008 | Link et al. |
| 2008/0009051 A1 | 1/2008 | Deutsch et al. |
| 2008/0063251 A1 | 3/2008 | Deutsch |
| 2008/0241874 A1 | 10/2008 | Deutsch |
| 2009/0105095 A1 | 4/2009 | Deutsch |
| 2009/0111141 A1 | 4/2009 | Deutsch |

FOREIGN PATENT DOCUMENTS

| | | |
|---|---|---|
| EP | 0059297 | 9/1982 |
| EP | 0094193 | 11/1983 |
| EP | 0602416 | 6/1994 |
| EP | 1262764 | 12/2002 |
| EP | 1566635 | 8/2005 |
| EP | 1691196 | 8/2006 |
| JP | 62-171687 | 7/1987 |
| JP | 06-221988 | 8/1994 |
| JP | 06-237753 | 8/1994 |
| JP | 10-276763 | 10/1998 |
| JP | 11-507724 | 7/1999 |
| JP | 2005-102628 | 4/2005 |
| WO | WO 96/31548 | 10/1996 |
| WO | WO 96/41153 | 12/1996 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 01/02539 | 1/2001 |

| WO | WO 01/35071 | 5/2001 |
| WO | WO 01/49824 | 7/2001 |
| WO | WO 01/88176 | 11/2001 |
| WO | WO 01/88185 | 11/2001 |
| WO | WO 02/26114 | 4/2002 |
| WO | WO 02/48676 | 6/2002 |
| WO | WO 02/055653 | 7/2002 |
| WO | WO 02/063034 | 8/2002 |
| WO | WO 02/064728 | 8/2002 |
| WO | WO 02/081662 | 10/2002 |
| WO | WO 02/097398 | 12/2002 |
| WO | WO 03/011451 | 2/2003 |
| WO | WO 03/035824 | 5/2003 |
| WO | WO 03/046508 | 6/2003 |
| WO | WO 03/052375 | 6/2003 |
| WO | WO 03/056330 | 7/2003 |
| WO | WO 03/056345 | 7/2003 |
| WO | WO 2004/077009 | 9/2004 |
| WO | WO 2004/113492 | 12/2004 |
| WO | WO 2005/007796 | 1/2005 |
| WO | WO 2005/069001 | 7/2005 |
| WO | WO 2005/103691 | 11/2005 |
| WO | WO 2006/003664 | 1/2006 |
| WO | WO 2006/021959 | 3/2006 |
| WO | WO 2006/043267 | 4/2006 |
| WO | WO 2006/080000 | 8/2006 |
| WO | WO 2007/052245 | 5/2007 |
| WO | WO 2007/074449 | 7/2007 |
| WO | WO 2009/063462 | 5/2009 |
| WO | WO 2009/081409 | 7/2009 |

OTHER PUBLICATIONS

Communication Pursuant to Article 94(3) EPC Dated Aug. 5, 2010 From the European Patent Office Re. Application No. 05757567.2.
Communication Pursuant to Article 94(3) EPC Dated Aug. 6, 2010 From the European Patent Office Re.: Application No. 04714873.9.
Communication Pursuant to Article 94(3) EPC Dated Aug. 9, 2010 From the European Patent Office Re. Application No. 01982673.4.
Communication Pursuant to Article 94(3) EPC Dated Feb. 13, 2009 From the European Patent Office Re.: Application No. 05763452.9.
Communication Pursuant to Article 94(3) EPC Dated Jun. 16, 2009 From the European Patent Office Re.: Application No. 04714873.9.
Communication Pursuant to Article 94(3) EPC Dated Feb. 29, 2008 From the European Patent Office Re.: 05763452.9.
Communication Pursuant to Rules 161(1) and 162 EPC Dated Aug. 25, 2010 From the European Patent Office Re. Application No. 08865081.7.
Communication Relating to the Results of the Partial International Search Dated May 20, 2009 From the International Searching Authority Re.: Application No. PCT/IL2008/001678.
International Preliminary Report on Patentability Dated Feb. 2, 2006 From the International Bureau of WIPO Re.: Application No. PCT/IL2004/000661.
International Preliminary Report on Patentability Dated May 3, 2007 From the International Bureau of WIPO Re.: Application No. PCT/IL2005/001078.
International Preliminary Report on Patentability Dated Mar. 8, 2007 From the International Bureau of WIPO Re.: Application No. PCT/IL2005/000914.
International Preliminary Report on Patentability Dated Aug. 9, 2007 From the International Bureau of WIPO Re.: Application No. PCT/IL2005/000801.
International Preliminary Report on Patentability Dated Jul. 10, 2008 From the International Bureau of WIPO Re.: Application No. PCT/IL2006/001487.
International Preliminary Report on Patentability Dated Jan. 18, 2007 From the International Bureau of WIPO Re.: Application No. PCT/IL2005/000719.
International Preliminary Report on Patentability Dated May 27, 2010 From the International Bureau of WIPO Re.: Application No. PCT/IL2008/001492.
International Preliminary Report on Patentability Dated May 27, 2010 From the International Preliminary Examining Authority Re.: Application No. PCT/IL2008/001678.
International Preliminary Report on Patentability Dated Nov. 28, 2007 From the International Bureau of WIPO Re.: Application No. PCT/IL2006/000483.
International Search Report Dated Mar. 2, 2005 From the International Searching Authority Re.: Application No. PCT/IL04/00661.
International Search Report Dated Feb. 7, 2006 From the International Searching Authority Re.: Application No. PCT/IL2005/001078.
International Search Report Dated Nov. 7, 2005 From the International Searching Authority Re.: PCT/IL2005/000801.
International Search Report Dated Nov. 9, 2004 From the International Searching Authority Re.: Application No. PCT/IL04/00571.
International Search Report Dated Sep. 10, 2009 From the International Searching Authority Re.: Application No. PCT/IL2008/001678.
International Search Report Dated Sep. 11, 2006 From the International Seaching Authority Re.: Application No. PCT/IL2006/000483.
International Search Report Dated May 13, 2009 From the International Searching Authority Re.: Application No. PCT/IL08/01492.
International Search Report Dated Nov. 15, 2005 From the International Searching Authority Re.: PCT/IL2005/000719.
International Search Report Dated Feb. 16, 2005 From the International Searching Authority Re.: PCT/IL04/00194.
International Search Report Dated Jan. 17, 2003 From the International Searching Authority Re.: Application No. PCT/IL01/00992.
International Search Report Dated Feb. 21, 2006 From the International Searching Authority Re.: Application No. PCT/IL2005/000914.
International Search Report Dated Sep. 21, 2007 From the International Searching Authority Re.: PCT/IL2006/001487.
International Search Report Dated Dec. 27, 2001 From the International Searching Authority Re.: Application No. PCT/IL01/00443.
Invitation to Pay Additional Fees Dated Mar. 3, 2009 From the International Searching Authority Re.: Application No. PCT/IL08/01492.
Notice of Allowance Dated Mar. 4, 2008 From the US Patent and Trademark Office Re.: U.S. Appl. No. 10/546,784.
Notice of Allowance Dated Jan. 7, 2008 From the US Patent and Trademark Office Re.: U.S. Appl. No. 10/938,951.
Notice of Allowance Dated Jan. 7, 2008 From the US Patent and Trademark Office Re.: U.S. Appl. No. 10/938,951.
Notice of Allowance Dated Jun. 15, 2010 From the US Patent and Trademark Office Re. U.S. Appl. No. 11/940,996.
Office Action Dated Jul. 1, 2010 From the Israeli Patent Office Re.: Application No. 172724 and Its Translation Into English.
Office Action Dated Mar. 8, 2006 From the Israeli Patent Office Re.: Application No. 138314.
Office Action Dated Apr. 12, 2007 From the Israeli Patent Office Re.: Application No. 138314.
Office Action Dated Jul. 14, 2009 From the Israeli Patent Office Re.: Application No. 172724 and Its Translation Into English.
Office Action Dated May 15, 2008 From the Israeli Patent Office Re.: Application No. 10/916,380.
Office Action Dated Jul. 19, 2006 From the Israeli Patent Office Re.: Application No. 138314.
Office Action Dated Mar. 22, 2009 From the Israeli Patent Office Re.: Application No. 170492 and Its Translation Into English.
Office Action Dated Sep. 29, 2003 From the Israeli Patent Office Re.: Application No. 136232.
Official Action Dated Sep. 2, 2010 From the US Patent and Trademark Office Re. U.S. Appl. No. 10/565,240.
Official Action Dated Feb. 5, 2007 From the US Patent and Trademark Office Re.: U.S. Appl. No. 10/916,380.
Official Action Dated Mar. 5, 2010 From the US Patent and Trademark Office Re.: U.S. Appl. No. 10/561,839.
Official Action Dated Sep. 10, 2010 From the US Patent and Trademark Office Re.: U.S. Appl. No. 11/646,317.
Official Action Dated Jul. 13, 2009 From the US Patent and Trademark Office Re.: U.S. Appl. No. 11/660,783.
Official Action Dated Dec. 14, 2007 From the US Patent and Trademark Office Re.: U.S. Appl. No. 10/916,380.

Official Action Dated Nov. 14, 2008 From the US Patent and Trademark Office Re.: U.S. Appl. No. 10/492,531.
Official Action Dated Sep. 14, 2010 From the US Patent and Trademark Office Re.: U.S. Appl. No. 11/631,737.
Official Action Dated Oct. 16, 2006 From the US Patent and Trademark Office Re.: U.S. Appl. No. 10/492,531.
Official Action Dated Aug. 17, 2010 From the US Patent and Trademark Office Re.: U.S. Appl. No. 10/561,839.
Official Action Dated Dec. 18, 2006 From the US Patent and Trademark Office Re.: U.S. Appl. No. 10/276,080.
Official Action Dated Feb. 19, 2008 From the US Patent and Trademark Office Re.: U.S. Appl. No. 10/492,531.
Official Action Dated Sep. 20, 2007 From the US Patent and Trademark Office Re.: U.S. Appl. No. 10/492,531.
Official Action Dated Oct. 22, 2007 From the US Patent and Trademark Office Re.: U.S. Appl. No. 11/492,531.
Official Action Dated Feb. 23, 2010 From the US Patent and Trademark Office Re.: U.S. Appl. No. 12/084,462.
Official Action Dated Mar. 23, 2005 From the US Patent and Trademark Office Re.: U.S. Appl. No. 10/276,080.
Official Action Dated Sep. 23, 2010 From the US Patent and Trademark Office Re.: U.S. Appl. No. 10/492,531.
Official Action Dated Sep. 23, 2010 From the US Patent and Trademark Office Re.: U.S. Appl. No. 11/646,294.
Official Action Dated Aug. 25, 2006 From the US Patent and Trademark Office Re.: U.S. Appl. No. 10/276,080.
Official Action Dated Jan. 25, 2007 From the US Patent and Trademark Office Re.: U.S. Appl. No. 10/492,531.
Official Action Dated Aug. 28, 2007 From the US Patent and Trademark Office Re.: U.S. Appl. No. 10/916,380.
Official Action Dated Jan. 28, 2010 From the US Patent and Trademark Office Re.: U.S. Appl. No. 10/492,531.
Official Action Dated Jun. 29, 2009 From the US Patent and Trademark Office Re.: U.S. Appl. No. 10/492,531.
Official Action Dated Sep. 29, 2010 From the US Patent and Trademark Office Re.: U.S. Appl. No. 11/883,028.
Response Dated Jun. 7, 2010 to Official Action of Mar. 5, 2010 From the US Patent and Trademark Office Re.: U.S. Appl. No. 10/561,839.
Response Dated Dec. 14, 2009 to Office Action of Jul. 14, 2009 From the Israel Patent Office Re.: Application No. 172724.
Response Dated Jun. 15, 2010 to Notice of Reason for Rejection of Mar. 30, 2010 From the Japanese Patent Office Re. Application No. 2006-502647.
Response Dated Sep. 21, 2010 to Communication Pursuant to Rules 161(1) and 162 EPC of Aug. 25, 2010 From the European Patent Office Re. Application No. 08865081.7.
Response Dated May 25, 2010 to Official Action of Jan. 28, 2010 From the US Patent and Trademark Office Re.: U.S. Appl. No. 10/492,531.
Response Dated Apr. 29, 2005 to Communication Pursuant to Article 96(2) EPC of Dec. 23, 2004 From the European Patent Office Re.: Application No. 01934272.4.
Response Dated Dec. 29, 2009 to Office Action of Sep. 2, 2009 From the Israel Patent Office Re.: Application No. 200559.
Response Dated Aug. 30, 2010 to Official Action of Jul. 13, 2009 From the US Patent and Trademark Office Re.: U.S. Appl. No. 11/660,783.
Response Dated Aug. 30, 2010 to Official Action of Feb. 23, 2010 From the US Patent and Trademark Office Re.: U.S. Appl. No. 12/084,462.
Supplementary European Search Report Dated Feb. 20, 2006 From the European Patent Office Re.: Application No. 04714873.9.
Supplementary European Search Report Dated Oct. 22, 2009 From the European Patent Office Re.: Application No. 04744911.1.
Supplementary European Search Report Dated Oct. 22, 2009 From the European Patent Office Re.: Application No. 04745001.0.
Supplementary European Search Report Dated Oct. 26, 2004 From the European Patent Office Re.: Application No. EP 01934272.
Translation of Notice of Reason for Rejection Dated Jul. 23, 2010 From the Japanese Patent Office Re.: Application No. 2006-502647.
Translation of Notice of Reason for Rejection Dated Nov. 27, 2007 From Japanese Patent Office Re.: Application No. 2003-538325.
Translation of Notice of Reason for Rejection Dated Mar. 30, 2010 From the Japanese Patent Office Re.: Application No. 2006-502647.
Written Opinion Dated Sep. 10, 2009 From the International Searching Authority Re.: Application No. PCT/IL2008/001678.
Written Opinion Dated May 13, 2009 From the International Searching Authority Re.: Application No. PCT/IL08/01492.
Written Opinion Dated Nov. 15, 2005 From the International Searching Authority Re.: Application No. PCT/IL2005/000719.
Aplin et al. "Protein-Derivatised Glass Coverslips for the Study of Cell-to-Substratum Adhesion", Analytical Biochemistry, 113: 144-148, 1981.
Arikawa et al. "Microbial Biosensors Based on Respiratory Inhibition", Methos in Biotechnology, 6(Chap.16): 225-235, 1998.
Baruch et al. "Enzyme Activity—Its All About Image", Trends in Cell Biology, 14(1): 29-35, 2004.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4—col. 2, §1, p. 8, col. 2, §2.
Burlage et al. "Living Biosensors for the Management and Manipulation of Microbial Consortia", Annual Reviews in Microbiology, 48: 291-309, 1994.
Craighead et al. "Textured Surfaces: Optical Storage and Other Applications", Journal of Vacuum Science and Technology 20 (3): 316, 1982. Abstract.
Darzynkiewicz et al. "Laser-Scanning Cytometry: A New Instrumentation With Many Applications", Experimental Cell Research, 249(1): 1-12, 1999. Abstract, p. 2, col. 2, §4—p. 4, col. 2, §2, p. 8, col. 1, §1—col. 2, §2.
Deutsch et al. "Apparatus for High-Precision Repetitive Sequential Optical Measurement of Living Cells", Cytometry, 16: 214-226, 1994.
Deutsch et al. "Microplate Cell-Retaining Methodology for High-Content Analysis of Individual Non-Adherent Unanchored Cells in A Population", Biomedical Microdevices, 8: 361-374, 2006.
Dive et al. "Improved Methodology for Intracellular Enzyme Reaction and Inhibition Kinetics by Flow Cytometry", Cytometry Journal of Society for Analytical Cytology, 8(6): 552-561, 1987.
Dolbeare "Fluorescent Staining of Enzymes for Flow Cytometry", Methods in Cell Biology, 33(Chap.8): 81-88, 1990.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3Fls%3D3%26nr%3D133&h=299&w=429&.
Eisenthal et al. "Infection of K562 Cells With Influenza A Virus Increases Their Susceptibility to Natural Killer Lysis", Pathobiology, 65: 331-340, 1997.
Hansen et al. "Quantification of Bioavailable Chlortetracycline in Pig Feces Using A Bacterial Whole-Cell Biosensor", Veterinary Microbiology, 87: 51-57, 2002.
Kiguchi et al. "Induction of Urokinase-Type Plasminogen Activator by the Anthracycline Antibiotic in Human RC-K8 Lymphoma and H69 Lung-Carcinoma Cells", International Journal of Cancer, 93: 792-797, 2001.
Klingel et al. "Flow Cytometric Determination of Serine Proteinase Activities in Living Cells With Rhodamine 110 Substrates", Methods in Cell Biology, 41(Chap.29): 449-460, 1994.
Koh et al. "Poly(Ethylene Glycol) Hydrogel Microstructures Encapsulating Living Cells", Langmuir, 18(7): 2459-2462, 2002. p. 2459-2462, Fig.3.
Kovacic et al. "Mechanisms of Carcinogenesis: Focus on Oxidative Stress and Electron Transfer", Current Medicinal Chemistry, 8: 773-796, 2001.
Lansing Taylor et al. "Real-Time Molecular and Cellular Analysis: The New Frontier of Drug Discovery", Current Opinion in Biotechnology, 12: 75-81, 2001.
Malin-Berdel et al. "Flow Cytometric Determination of Esterase and Phosphatase Activities and Kinetics in Hematopoietic Cells With Fluorogenic Substrates", Cytometry, 1(3): 222-228, 1980.

Mrksich et al. "Using Self-Assembled Monolayers to Understand the Interactions of Man-Made Surfaces With Proteins and Cells", Annual Reviews in Biophysics and Biomolecular Structure, 25: 55-78, 1996.

Nooter et al. "On-Line Flow Cytometry. A Versatile Method for Kinetic Measurement", Methods in Cell Biology, 41(Chap.32): 509-526, 1994.

Riedel et al. "Arxula Adeninivorans Based Sensor for the Estimation of Bod", Analytical Letters, 31(1): 1-12, 1998.

Schroeder et al. "Coordination of Cell Growth in Cocultures by A Genetic Proliferation Control System", Biotechnology and Bioengineering, 78(3): 346-352, 2002.

Seahorse Bioscience "Designed for Scientists by Scienctists. How the XF24 Extracellular Flux Analyzer Works", Product Description, Seahorse Bioscience, 4 P., 2008.

Seahorse Bioscience "XF24 Extracellular Flux Analyzer", Product Description, Seahorse Bioscience, 3 P., 2008.

Simonian et al. "Microbial Biosensors Based on Potentiometric Detection", Methods in Biotechnology, 6(Chap.17): 237-248, 1998.

Singhvi et al. "Engineering Cell Shape and Function", Science, 264: 696-698, 1994.

Stevens et al. "Quorum Sensing in Vibrio Fischeri: Essential Elements for Activation of the Luminescence Genes", Journal of Bacteriology, 179(2): 557-562, Jan. 1997.

Suehiro et al. "The Dielectrophoretic Movement and Positioning of A Biological Cell Using A Three-Dimensional Grid Electrode System", J. Phys. D. Appl. Phys, vol. 31 p. 3298-3305, 1998.

Sunray et al. "Cell Activation Influences Cell Staining Kinetics", Spectrochimica Part A, 53: 1645-1653, 1997.

Sunray et al. "Determination of Individual Cell Michaelis-Menten Constants", Cytometry, 47(1): 8-16, 2002.

Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.

Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7—p. 714, col. 2, §1.

Tixier et al. Catching and Attaching Cells Using An Array of Microholes, Abstract of the 2nd Conference of the Society for Chemistry and Micro Systems, p. 60, 2000.

Turek et al. "Leucine Aminopeptidase Activity by Flow Cytometry", Methods in Cell Biology, 41(Chap.30): 461-468, 1994.

Watson et al. "Enzyme Kinetics", Methods in Cell Biology, 41: 469-508, 1994.

Yamamura et al. "Single-Cell Microarray for Analyzing Cellular Response", Analytical Chemistry, 77(24): 8050-8056, 2005.

Official Action Dated Oct. 27, 2010 From the US Patent and Trademark Office Re.: U.S. Appl. No. 12/890,668.

Official Action Dated Nov. 1, 2010 From the US Patent and Trademark Office Re.: U.S. Appl. No. 11/883,028.

Official Action Dated Dec. 9, 2010 From the US Patent and Trademark Office Re. U.S. Appl. No. 10/565,240.

Official Action Dated Dec. 22, 2010 From the US Patent and Trademark Office Re.: U.S. Appl. No. 11/883,028.

Response Dated Jan. 2, 2011 to Proceeding Further With the European Patent Application Pursuant to Rule 70(2) EPC of Nov. 10, 2009 From the European Patent Office Re. Application No. 04745001.0.

Response Dated Nov. 8, 2010 to Official Action of Sep. 10, 2010 From the US Patent and Trademark Office Re.: U.S. Appl. No. 11/646,317.

Response Dated Nov. 15, 2010 to Official Action Dated Sep. 14, 2010 From the US Patent and Trademark Office Re.: U.S. Appl. No. 11/631,737.

Response Dated Nov. 15, 2010 to Official Action of Nov. 1, 2010 From the US Patent and Trademark Office Re.: U.S. Appl. No. 11/883,028.

Response Dated Dec. 16, 2010 to Official Action of Aug. 17, 2010 From the US Patent and Trademark Office Re.: U.S. Appl. No. 10/561,839.

Response Dated Dec. 20, 2010 to Official Action of Sep. 23, 2010 From the US Patent and Trademark Office Re.: U.S. Appl. No. 10/492,531.

Response Dated Nov. 30, 2010 to Communication Pursuant to Article 94(3) EPC of Aug. 5, 2010 From the European Patent Office Re. Application No. 05757567.2.

Official Action Dated Jan. 19, 2011 From the US Patent and Trademark Office Re.: U.S. Appl. No. 11/646,317.

Response Dated Jan. 24, 2011 to Official Action of Sep. 23, 2010 From the US Patent and Trademark Office Re.: U.S. Appl. No. 11/646,294.

Communication Pursuant to Rule 58 EPC or Rule 159 EPC Dated Nov. 24, 2010 From the European Patent Office Re. Application No. 10183774.8.

Response Dated Jan. 3, 2011 to Communication Pursuant to Rule 58 EPC or Rule 159 EPC of Nov. 24, 2010 From the European Patent Office Re. Application No. 10183774.8.

Response Dated Jan. 12, 2011 to Office Action of Oct. 5, 2010 From the Israel Patent Office Re. Application No. 184818.

Official Action Dated Feb. 1, 2011 From the US Patent and Trademark Office Re.: U.S. Appl. No. 11/631,737.

Office Action Dated Oct. 5, 2010 From the Israel Patent Office Re. Application No. 184818 and Its Translation Into English.

Response Dated Oct. 4, 2010 to Official Action of Sep. 2, 2010 From the US Patent and Trademark Office Re. U.S. Appl. No. 10/565,240.

Response Dated Oct. 10, 2010 to Notice of Reason for Rejection of Jul. 23, 2010 From the Japanese Patent Office Re.: Application No. 2006-502647.

Interview Summary Dated Feb. 11, 2011 From the US Patent and Trademark Office Re.: U.S. Appl. No. 11/883,028.

Response Dated Feb. 7, 2011 to Communication Pursuant to Article 94(3) EPC of Aug. 6, 2010 From the European Patent Office Re.: Application No. 04714873.9.

Office Action Dated Feb. 28, 2011 From the Israel Patent Office Re. Application No. 180568 and its Translation Into English.

Official Action Dated Mar. 9, 2011 From the US Patent and Trademark Office Re.: U.S. Appl. No. 11/660,783.

Response Dated Mar. 22, 2011 to Official Action of Dec. 22, 2010 From the US Patent and Trademark Office Re.: U.S. Appl. No. 11/883,028.

Invitation Pursuant to Article 94(3) and Rule 71(1) EPC Dated Apr. 8, 2011 From the European Patent Office Re. Application No. 01982673.4.

Official Action Dated 16 Mar. 2011 From the US Patent and Trademark Office Re. Application No. 10/561,839.

Official Action Dated 31 Mar. 2011 From the US Patent and Trademark Office Re.: Application No. 10/492,531.

Response Dated Feb. 17, 2011 to Communication Pursuant to Article 94(3) EPC of Aug. 9, 2010 From the European Patent Office Re. Application No. 01982673.4.

Response Dated Feb. 23, 2011 to Official Action of Jan. 19, 2011 From the US Patent and Trademark Office Re.: Application No. 11/646,317.

Cornell University "All About Birds: Optical Quality", Cornell University, 2 p., Oct. 3, 2010.

Invitation Pursuant to Rule 63(1) EPC Dated May 3, 2011 From the European Patent Office Re. Application No. 10183774.8.

Official Action Dated Apr. 15, 2011 From the US Patent and Trademark Office Re.: Application No. 12/084,462.

Official Action Dated Apr. 22, 2011 From the US Patent and Trademark Office Re.: Application No. 11/646,294.

Notice of Allowance Dated Jun. 9, 2011 From the US Patent and Trademark Office Re.: Application No. 11/883,028.

Notification of European Publication No. And Information on the Application of Article 67(3) EPC Dated May 18, 2011 From the European Patent Office Re. Application No. 10183774.8.

Official Action Dated May 23, 2011 From the US Patent and Trademark Office Re.: Application No. 11/646,317.

Response Dated May 31, 2011 to Invitation Pursuant to Article 94(3) and Rule 71(1) EPC of Apr. 8, 2011 From the European Patent Office Re. Application No. 01982673.4.

PICO LITER WELL HOLDING DEVICE AND METHOD OF MAKING THE SAME

CROSS-REFERENCE TO RELATED APPLICATIONS

This application is a continuation of U.S. patent application Ser. No. 11/940,996, filed Nov. 15, 2007, which is a continuation-in-part of U.S. patent application Ser. No. 10/561,839, filed Jun. 5, 2006, which is a National Phase of International Application No. PCT/IL04/000571, filed Jun. 27, 2004, claims the benefit of U.S. Provisional Patent Application Nos. 60/544,357, filed Feb. 17, 2004, 60/544,356, filed Feb. 17, 2004, 60/517,073, filed Nov. 5, 2003, 60/517,084, filed Nov. 5, 2003, 60/488,408, filed Jul. 21, 2003, and 60/482,437, filed Jun. 26, 2003.

U.S. patent application Ser. No. 11/940,996, is also a continuation-in-part of International Application No. PCT/IL06/001487, filed Dec. 26, 2006, which claims the benefit of U.S. Provisional Patent Application No. 60/754,216, filed Dec. 28, 2005.

The contents of all of the above applications are incorporated by reference as if fully set forth herein.

STATEMENT REGARDING FEDERALLY SPONSORED RESEARCH OR DEVELOPMENT

None.

REFERENCE TO A "SEQUENCE LISTING"

None.

TECHNICAL FIELD

The present invention relates to devices that include pico liter wells used in the study of cellular biology. More specifically, the present invention relates to holding devices having a multiplicity of pico liter wells formed in a substrate having a refractive index similar to that of water, and methods of making the same.

BACKGROUND OF THE INVENTION

In the study of cellular biology, biochemistry, pharmacology, immunology, and other biological science related fields, it is desirable to study whole, living, individual and small groups of cells, by manipulating and isolating the cells. Thus, it is desirable to provide holding devices having surfaces comprising a multiplicity of pico liter wells so that cells being observed may be isolated from one another in the pico liter wells enabling single cells to be observed.

Heretofore, while holding devices which have substrates with pico liter wells formed in the substrate surface to trap individual cells have been available, it has been difficult to directly observe the cells as precisely as desirable because of optical artifacts caused by the differences between the refractive indices of the medium carrying the cells and the material forming the pico liter wells. These artifacts are caused by the refraction of light passing from the substrate to the cell carrying medium.

Most commonly, aqueous buffers comprised largely of water are used as a medium for carrying cells to be observed. It is therefore desirable to provide pico liter wells in a surface that has optical characteristics as close to that of water as possible, and more specifically, it is desirable to provide a substrate in which pico liter wells can be formed and that has a refractive index very close to or the same as water.

SUMMARY OF THE INVENTION

It is therefore an object of the invention to provide a holder device having at least one cavity for receiving a sample of cells in a medium, wherein the at least one cavity includes a substrate having refractive index substantially equal to that of water, includes a multiplicity of pico liter wells formed therein and has a generally inert wall.

It is another object of the invention to provide a method of making a holding device having a substrate characterized by an index of refraction essentially equal to that of water, which is adhered to a carrier plate, wherein the substrate is formed into a multiplicity of pico liter wells.

It is another object of the invention to provide a method of making a holding device having at least one cavity for receiving a medium, wherein the at least one cavity has a multiplicity of pico liter wells formed in a substrate having a refractive index substantially equal to the medium in which the cells are carried.

A holding device for studying cells in a medium in accordance with this invention comprises at least one cavity defined by generally inert wall surrounding a substrate. The substrate has a surface in which a plurality of pico liter wells is formed. The substrate is translucent and has a refractive index substantially equal to the refractive index of the medium.

A preferred holding device for studying cells in accordance with this invention comprises a substantially transparent substrate having a refractive index of 1.33. The substrate has a multiplicity of pico liter wells formed in an upper surface and a wall structure attached thereto.

In another embodiment, the present invention includes a holding device for studying cells comprising a substantially transparent carrier plate having a plurality of cavities surrounded by walls formed in a first surface of the carrier plate, a layer of adhesive, which is known to those skilled in the art, disposed on a bottom surface of each cavity, a layer of substantially transparent substrate material having a refractive index of 1.33 and having a multiplicity of pico liter wells formed in an upper surface thereof disposed on the adhesive layer. While MY-133 is known to have a refractive index close to that of water, heretofore MY-133 has not been considered suitable for use as an inert substrate for holding live cells in a medium.

The invention further includes a method of making a holding device for studying cells comprising the steps of providing a layer of curable substrate, disposing a wall structure on the layer of curable substrate, embossing a multiplicity of pico liter wells in a surface of the curable substrate, and curing the substrate.

The invention further includes a method of making a holding device for studying cells comprising the steps of providing a carrier plate, applying a first adhesive layer to the carrier plate, depositing a curable substrate on the adhesive layer, applying a second layer of adhesive to the substrate, attaching a wall structure to the second layer of the adhesive, forming a multiplicity of pico liter wells in the substrate with a template, curing the substrate, and removing the template.

The invention also includes a method of making a holding device comprising the steps of providing a carrier plate having a plurality of cavities surrounded by walls, depositing a curable substrate in each cavity, embossing a multiplicity of pico liter wells in the curable substrate with a die, and curing the substrate.

The novel aspects of the invention are set forth with particularity in the appended claims. The invention itself, together with further objects and advantages thereof, may be more readily comprehended by reference to the following detailed description of a presently preferred embodiment of the invention taken in conjunction with the accompanying drawings in which:

BRIEF DESCRIPTION OF THE DRAWING FIGURES

DETAILED DESCRIPTION OF THE INVENTION

At the outset, it should be appreciated that the use of the same reference number throughout the several figures designates a like or similar element.

Figure 1:
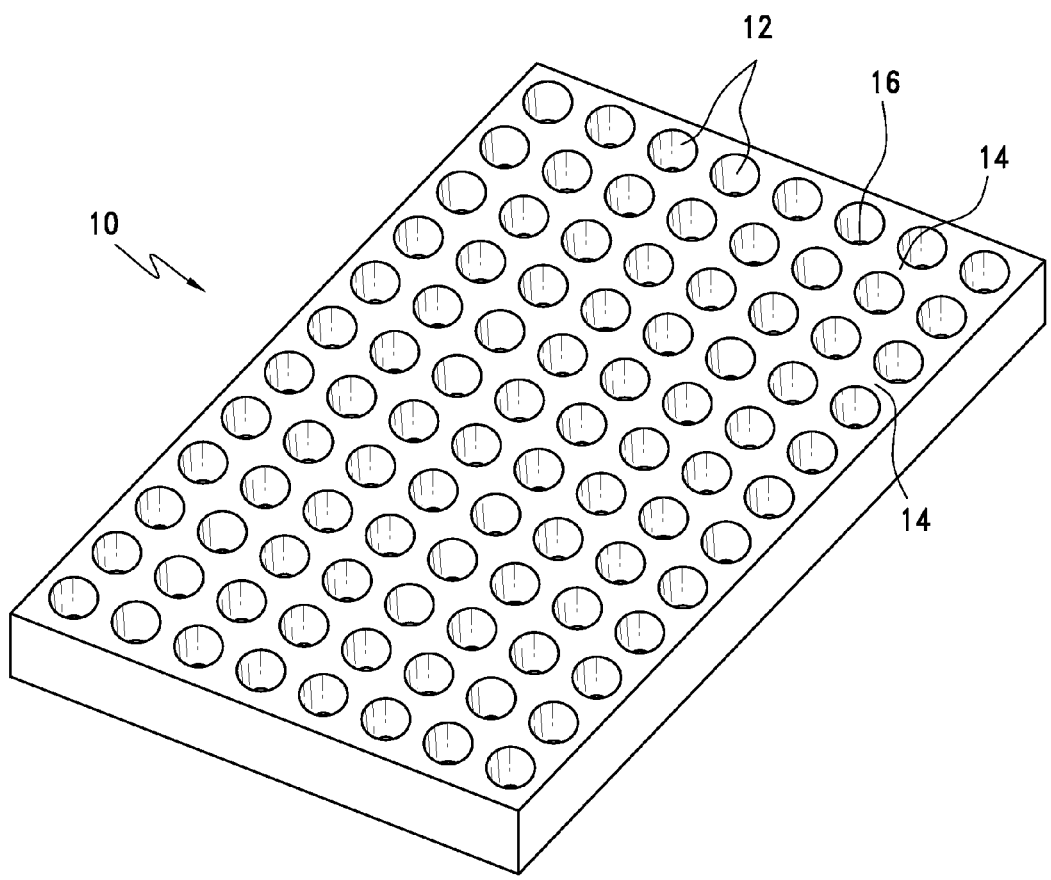
FIG. 1 is a perspective view of a presently preferred embodiment of a holding device.

Referring now to the figures, FIG. 1 is a perspective view of a holding device 10 having at least one cavity 12. Holding device 10 may be a Petri dish or similar device, or an assay plate having 6, 12, 48, 96, 384, or 1536 cavities and a standard 8.5 cm by 12.5 cm footprint. The cavity or plurality of cavities 12 is configured to receive aliquots of cells that are temporarily suspended in a desired medium, such as a buffered medium comprising mostly water. The diameter of the individual cavities 12 depends on the number of wells included on the holding device 10. Preferably, the cavities 12 of a 1536 well plate have a diameter greater than approximately 250 micrometers. It should be apparent that the volume of the cavities 12 also depends on the number of cavities and on the depth of each cavity. Generally, the volume of each cavity is greater than $5 \times 10^{-6}$ liters.

Figure 9:
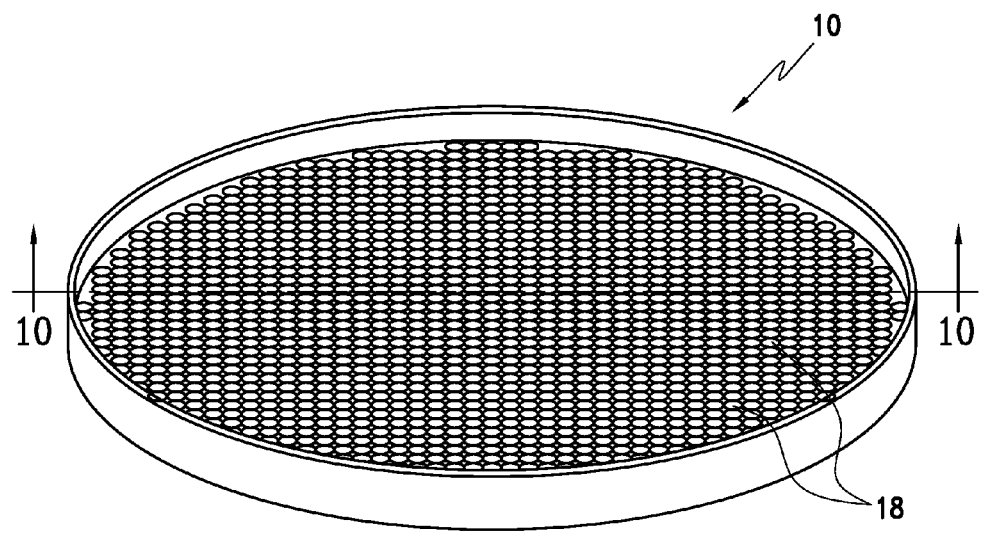
FIG. 9 is a perspective view of a petri-dish having the plurality of pico liter wells formed in the substrate.

The cavities 12 further include generally inert walls 14 (also referred to hereinafter as a plurality of walls or a wall structure) and a bottom substrate 16 having a multiplicity of pico liter wells 18 (as shown in FIG. 9). Preferably, the pico liter wells 18 are configured to physically confine individual cells or a group of cells, wherein the diameter of the pico liter wells 18 depends on the size of the cells to be used. For example, the cells preferably have a diameter between about 5 and 250 micrometers and the pico liter well size and shape may correspond thereto.

In an embodiment of the invention, the substrate 16 is curable, moldable and inert. The substrate 16 in the cured state has an index of refraction of 1.33, which has the substantially same index of refraction as water and approximately the same index of refraction of most mediums used for suspending cells. Preferably, the substrate 16 is MY-133, which is a commercially available material and can be purchased at My Polymers LTD at http://www.mypolymers.com/Default.htm.

Figure 2:
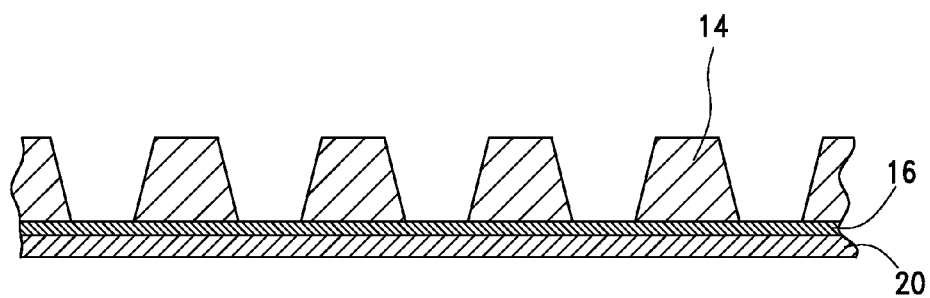
FIG. 2 is a cross-sectional view of a carrier plate having a substrate and a plurality of walls.
Figure 3:
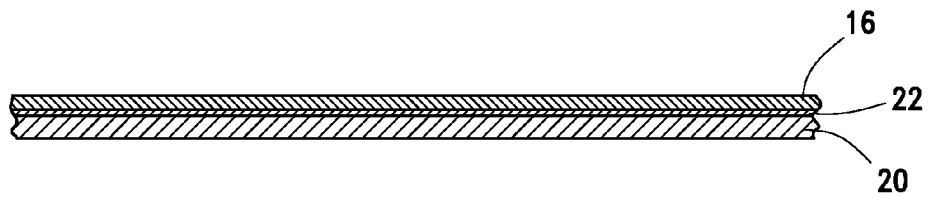
FIG. 3 is a cross-sectional view of the carrier plate having a first adhesive and the substrate applied thereon.

As shown in FIG. 2, in an embodiment of the invention, the substrate 16 is applied to a carrier plate 20, preferably by brushing, stamping or printing the substrate 16 thereon. The carrier plate 20 is preferably made from glass or another optically transmissive material such as polystyrene or the like.

In order to improve the adherence of the substrate 16 to the glass carrier plate 20, the carrier plate 20 is preferably pretreated with silane before the substrate 16 is applied. The silanation of the surface of the carrier plate 20 can be performed in a manner known to one skilled in the art. Through such silanation process, acrylic groups are attached by covalent bonds to the glass, improving the adhesion of the substrate 16 to the glass carrier 20.

The substrate 16 forms a layer, which may have a thickness of less than 200 microns and more preferably in the range of 80-120 microns. The plurality of walls 14 is then disposed on the substrate 16.

Pico liter well forming templates 26 are disposed between each set of plurality of walls 14 disposed on the substrate 16 layer and are pressed into the substrate 16. The templates 26 are preferably dies capable of embossing the substrate 16 with pico liter sized wells. The layered configuration, including the carrier plate 20, the substrate 16, the templates 26 pressed into the substrate 16, and the plurality of walls 14 is polymerized by UV-radiation to cure the substrate 16. Preferably, the layered configuration is irradiated with UV-light through the bottom of the translucent carrier plate 20. The templates 26 are then preferably removed and the holding device 10 is cured again by irradiating the holding device 10 with UV-light under a vacuum of 0.3-0.5 mmHg.

In an alternative embodiment of the invention, as shown in FIGS. 3-6, the holding device 10 includes at least a first adhesive 22 applied between the carrier plate 20 and the substrate 16 to further improve bonding of the substrate 16 thereto. Additionally, a second adhesive 24 may be applied to further improve bonding of the plurality of walls 14 to the substrate 16. This holding device 10 and method of making the same is described herebelow.

In order to improve the adherence of the adhesive 22 to the glass carrier plate 20, the carrier plate 20 is preferably pretreated with silane before the first adhesive 22 is applied. The silanation of the surface of the carrier plate 20 can be performed in a manner known to one skilled in the art. Through such silanation process, acrylic groups are attached by covalent bonds to the glass, improving the adhesion of the first adhesive 22 to the glass carrier 20.

A thin coat of the first adhesive 22 is applied to the carrier plate 20, preferably, by brushing the adhesive 22 thereon. It should be apparent, however, that other techniques may be used to apply the first adhesive 22, such as by stamping, printing, spraying, dipping, wiping, or the like. Preferably, the adhesive 22 is applied to only those locations that correspond to the locations of the plurality of walls 14, such that the transparency of the bottom of each cavity 12 is not affected by the adhesive 22. However, in an embodiment of the invention, the adhesive 22 comprises mostly MY-133 and can be applied to the entire surface of the carrier plate 20 because the adhesive 22 also has substantially the same refractive index as water. The adhesive 22 can be any type of adhesive that bonds to the substrate as described below. Preferably, the first adhesive is a viscous primer that does not mix into a substrate 16. More specifically, the first adhesive 22 is applied as a dilute solution of 25% solids in a mixture based on a medium boiling solvent, wherein the solvent evaporates leaving a thin, but highly viscous layer of adhesive 22 on the carrier plate 20. The solvent preferably comprises PCBTF (also know by the trade name of Oxsol 100), having a boiling point of 139 degrees, isopropyl alcohol (IPA) and acetone. Preferably the adhesive 22 is an ultraviolet (UV) radiation curable formulation which adheres well to the substrate 16 and the carrier plate 20. Preferably, the adhesive 22 is selected so that it is polymerized together with the substrate 16 when exposed to ultraviolet radiation. More specifically, the adhesive 22 is applied to the carrier plate 20 and the substrate 16 is applied over the adhesive 22, the combination polymerized by UV-radiation at the same time.

Further coats of the adhesive 22 can be applied to the first coat of the adhesive 22 and each coat is allowed to dry for at least 2-4 minutes.

The substrate 16 is applied to the adhesive 22 coated surface of the carrier plate 20 and is formed from a moldable, preferably UV curable material having an index of refraction substantially the same as the index of refraction of a buffered, substantially water-based medium. The substrate 16 forms a layer, which may have a thickness of less than 200 microns and more preferably in the range of 80-120 microns.

Preferably, when the substrate 16 is formed from MY-133, an adhesive comprises a polymer that preferably includes both acrylic groups and highly fluorinated groups that attract the components of the MY-133. Where a glass carrier plate 20 is used, it is desirable to modify the first adhesive 22 to increase its affinity for glass. The adhesive 22 thus, may include 1-2% additional silane.

A second adhesive 24 is applied to the bottom of the plurality of walls 14 arranged to define cavities 12 of the holding device 10 and the plurality of walls 14 are then disposed onto the substrate 16. The second adhesive 24 is allowed to dry for at least 2-4 minutes. Similar to the first adhesive 22, the second adhesive 24 is also a viscous primer that does not mix into a substrate 16. More specifically, the second adhesive 24 is applied as a dilute solution of 25% solids in a mixture based on a medium boiling solvent, wherein the solvent evaporates leaving a thin, but highly viscous layer of adhesive 24 on the bottom of the plurality of walls 14. The solvent preferably comprises PCBTF (also known by the trade name Oxsol 100), having a boiling point of 139 degrees, isopropyl alcohol (IPA) and acetone. Preferably the adhesive 24 is an UV-radiation curable formulation which adheres well to the substrate 16 and the plurality of walls 14. Preferably, the adhesive 24 is selected so that it is polymerized together with the substrate 16 when exposed to ultraviolet radiation. This permits the adhesive 24 to be applied to the bottom of the plurality of walls 14, which is then attached to the substrate 16 layer adhered to the carrier plate 20 by the first adhesive 22.

It should be appreciated by those having ordinary skill in the art that although the above-described adhesives are preferred, other adhesives that are capable of bonding to the substrate 16 can be used.

Figure 4:
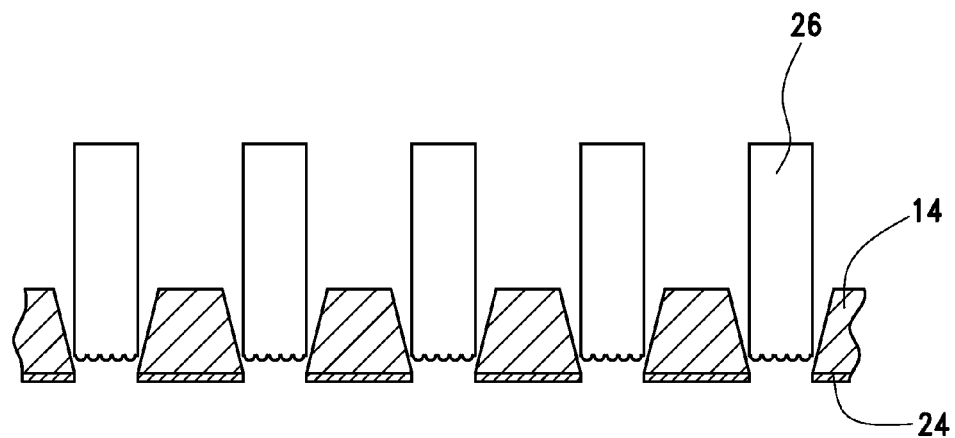
FIG. 4 is a cross-sectional view of the plurality of walls and templates.
Figure 5:
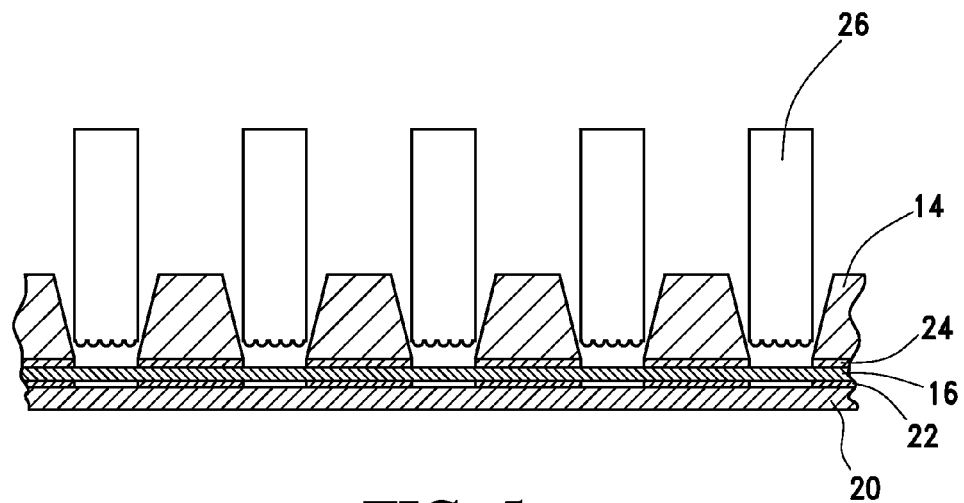
FIG. 5 is a cross-sectional view of the holding device showing the plurality of walls mounted on the carrier plate and showing dies embossing a plurality of pico liter wells in the substrate.
Figure 6:
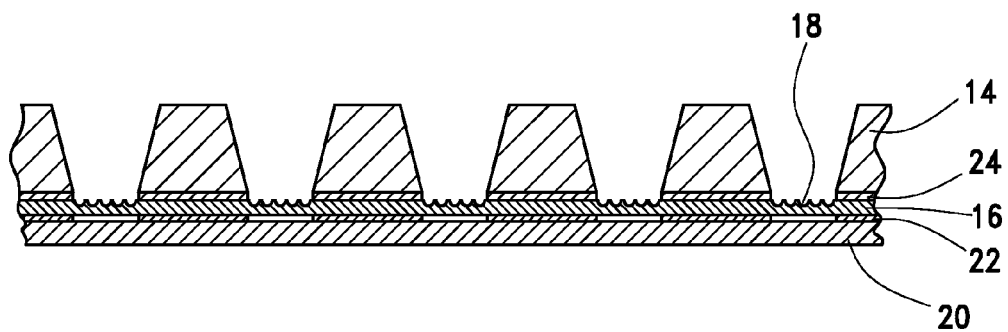
FIG. 6 is a cross-sectional view of the holding device showing the pico liter wells embossed in the substrate.

As shown in FIGS. 4 and 5, pico liter well forming templates 26 are disposed between each set of plurality of walls 14 disposed on the substrate 16 layer and are then pressed into the substrate 16. The templates 26 are preferably dies capable of embossing the substrate 16 with pico liter sized wells. The layered configuration, including the carrier plate 20, first adhesive 22, substrate 16, template pressed into the substrate 16, and plurality of walls 14 is polymerized by UV-radiation to cure the substrate 16 and the adhesives 22, 24 at the same time. Preferably, the layered configuration is irradiated with UV-light through the bottom of the translucent carrier plate 20. The templates 26 are then preferably removed and the holding device 10 is cured again by irradiating the holding device 10 with UV-light under vacuum of 0.3-0.5 mmHg.

Figure 7:
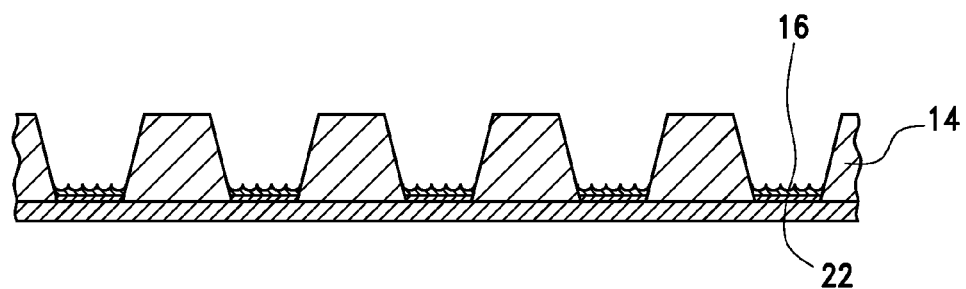
FIG. 7 is a cross-sectional view of the holding device showing the first adhesive and the substrate applied to the bottom of cavities.
Figure 8:
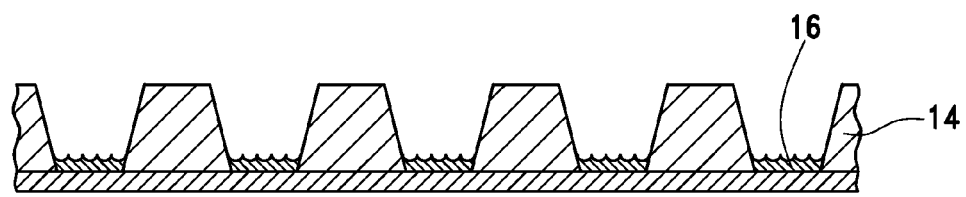
FIG. 8 is a cross-sectional view of the holding device showing the substrate applied to the bottom of the cavities.

Another method of making the invention includes providing a carrier 20 having at least one cavity 12 surrounded by walls 14. As shown in FIG. 7, a layer of either the first or second adhesive 22, 24, respectively, is deposited at the bottom of the at least one cavity 12. A layer of substrate 16 is then applied to the adhesive layer 22 or 24. The layer of substrate 16 can also be applied directly to the bottom of the at least one cavity 12, without the adhesive 22 or 24 as shown in FIG. 8. The pico liter well templates 26 are then translated between the walls 14 and pressed into the substrate 16 to emboss the pico liter wells 18. The first or second adhesive 22 or 24, if present, and the substrate 16 are cured by UV-radiation through the bottom of the holding device 10. Then, the templates 26 are removed and the holding device 10 undergoes further curing by UV-light under vacuum of 0.3-0.5 mmHg or inert gas.

Figure 10:
FIG. 10 is a cross-sectional view of the petri-dish having the plurality of pico liter wells formed in the substrate.

In yet another embodiment of the invention, the carrier plate 20 is not utilized. That is, the holding device 10 can include the substrate 16 embossed to form pico liter wells 18 as described above and shown in FIGS. 9 and 10. The substrate 16 preferably has a thickness of less than 200 microns and more preferably in the range of 80-120 microns. The walls 14 are disposed on the substrate 16 and templates 26 are pressed into the substrate 16. While the templates remain pressed into the substrate 16, the substrate 16 is cured with UV-radiation. The templates 26 are removed and the substrate 16 can optionally be cured again, but with UV-radiation under vacuum.

In yet a further embodiment of the invention, the walls 14 can be disposed on the substrate 16 after the UV-curing thereof. The walls 14 are then affixed along a perimeter edge of the substrate 16 using any type of strong adhesive known in the art. According to one aspect of the invention, the perimeter of the walls 14 can be adhered to the edge of the substrate 16 forming a Petri dish-shaped holding device 10.

Alternatively, the walls 14 having adhesive 22 or 24 can be applied to a layer of substrate 16, wherein the substrate 16 functions as the bottom of the holding device 10. The templates 26 are pressed into the substrate 16 to emboss the pico liter wells 18 therein. The layered configuration, including the templates 26, is cured using UV-radiation. It should be appreciated by one having ordinary skill in the art that, since the holding device 10 does not include the carrier plate 20 attached to the substrate 16 via adhesive 22 or 24, the holding device 10 can be cured from above the substrate 16 or below the substrate 16. After the first curing step, the template 16 is removed and the holding device 10 is then cured again, using UV-light under vacuum. Thereafter, the pico liter well holding device 10 is sterilized for use in biological experiments.

In use, holding device 10 is seeded with cells, for example by injecting cells suspended in a medium, such as an aqueous buffered medium, into at least a first cavity of the holding device 10. The device 10 is agitated to ensure that the cells settle in the pico liter wells 18. The cells are then observed from below, for example, using a confocal microscope or brightfield microscope with or without deconvolution image processing software. Because the substrate 16 has a refractive index of water, optical artifacts, which are caused by the differences between the refractive indices of the medium carrying the cells and the substrate 16, are essentially eliminated. This gives the viewer the ability to observe the cells being studying more precisely as if there were no microstructures on the substrate.

There has thus been described a method of making a holding device for studying cells and apparatus used in conjunction with the above described methods. Those skilled in the art will recognize that modifications may be made in the method and apparatus described herein without departing from the true spirit and scope of the invention which accordingly are intended to be limited solely by the appended claims.

The invention claimed is:

1. A holding device for studying cells comprising:
at least one cavity adapted to receive a sample of cells in a medium consisting essentially of water, the cavity having a substrate, wherein the substrate includes a surface for receiving the medium, and wherein the surface includes a multiplicity of pico liter wells and is characterized in that the substrate is substantially translucent and has a refractive index equal to the refractive index of the medium.

2. The holding device of claim 1, wherein the medium comprises water and wherein the substrate has a Refractive Index of 1.33.

3. The holding device of claim 1, wherein the substrate is moldable.

4. The holding device of claim 1, wherein the substrate is inert.

5. The holding device of claim 1, wherein the holding device is a carrier plate, and wherein a first adhesive is disposed between the carrier plate and the substrate.

6. The holding device of claim 5, wherein at least one of the substrate, and the first adhesive are UV-light curable.

7. The holding device of claim 5, wherein the first adhesive is an acrylic.

8. The holding device of claim 6, further including a light source transmitting the UV-light through a bottom surface of the at least one cavity.

9. The holding device of claim 8, wherein the substrate is exposed to the UV-light under vacuum pressure.

10. The holding device of claim 9, wherein the vacuum pressure is in the range of 0.3-0.5 mmHg.

11. The holding device of claim 8, wherein the substrate is exposed to the UV-light under inert gas.

12. The holding device of claim 1 including an adhesive disposed between a generally inert wall and the substrate.

13. The holding device of claim 12 wherein the adhesive is UV-light curable.

14. The holding device of claim 12 wherein the adhesive is an acrylic.

15. A method of making a holding device for studying cells, comprising the steps of:
providing a carrier plate;
forming a multiplicity of pico liter wells in a substrate with a template;
curing the substrate; and
removing the template.

16. The method according to claim 15, in which the step of curing the substrate includes exposing the substrate to UV-light through the carrier plate.

17. The method according to claim 15, further comprising repeating the step of curing the substrate after removing the template, wherein the step of curing the substrate after removing the template includes exposing the substrate to UV-light under a vacuum pressure through the carrier plate.

18. The method according to claim 15, in which the step of forming a multiplicity of pico liter wells in the substrate with a template further comprises embossing a surface of the substrate with a die.

19. The method according to claim 15 further comprising applying an adhesive layer to the carrier plate.

20. The method according to claim 19 comprising depositing the cured substrate on the adhesive layer.

21. The method according to claim 20 comprising applying a second adhesive layer to the substrate.

22. The method according to claim 21 comprising attaching a wall structure to the second adhesive layer.

23. A method of making a holding device, comprising the steps of:
providing a layer of curable substrate;
embossing a multiplicity of pico liter wells in a surface of the curable substrate; and
curing the substrate.

24. The method according to claim 23, further comprising the step of disposing a first adhesive between the curable substrate and a wall structure.

25. The method according to claim 23, in which the step of curing the substrate comprises exposing the substrate to the UV-light through the carrier.

26. The method according to claim 23, further comprising disposing a wall structure on the layer of curable substrate.

* * * * *